United States Patent
Chien et al.

(10) Patent No.: US 6,815,160 B1
(45) Date of Patent: Nov. 9, 2004

(54) HEPATITIS C VIRAL ANTIGEN IMMUNOASSAY DETECTION SYSTEMS

(75) Inventors: David Y. Chien, Alamo, CA (US); Phillip Arcangel, Oakland, CA (US)

(73) Assignee: Chiron Corporation, Emeryville, CA (US)

( * ) Notice: Subject to any disclaimer, the term of this patent is extended or adjusted under 35 U.S.C. 154(b) by 256 days.

(21) Appl. No.: 10/048,191

(22) PCT Filed: Jul. 25, 2000

(86) PCT No.: PCT/US00/20214

§ 371 (c)(1),
(2), (4) Date: Jan. 25, 2002

(87) PCT Pub. No.: WO01/09609

PCT Pub. Date: Feb. 8, 2001

Related U.S. Application Data

(60) Provisional application No. 60/146,079, filed on Jul. 28, 1999.

(51) Int. Cl.$^7$ .................................................. C12Q 1/70
(52) U.S. Cl. ............................................. 435/5; 435/7.2
(58) Field of Search ....................................... 435/5, 7.2

(56) References Cited

U.S. PATENT DOCUMENTS 4,464,474 A    8/1984   Coursaget et al.

FOREIGN PATENT DOCUMENTS

| FR | 2502154 A | 9/1982 |
|---|---|---|
| WO | WO 92/13892 A1 | 8/1992 |
| WO | WO 93/04205 A1 | 3/1993 |
| WO | WO 93/06488 A1 | 4/1993 |
| WO | WO 94/01778 A1 | 1/1994 |
| WO | WO 97/40176 A1 | 10/1997 |
| WO | WO 99/15898 A1 | 4/1999 |

OTHER PUBLICATIONS

Cardoso et al (Journal of Medical Virology 55:28–34, 1998).*

Reesink et al (Dev. Biol. Stand. 81:77–84, 1993).*

Deleersnyder et al (Journal of Virology 71:697–704, 1997).*

Pawlotsky (Journal of Hepatology 31 (Suppl. 1): 71–79, 1999).*

Aoyagi et al (J. Clin. Microbiol. 37:1802–1808, 1999).*

* cited by examiner

Primary Examiner—Mary E. Mosher
(74) Attorney, Agent, or Firm—Alisa A. Harbin; Roberta L. Robins; Robert P. Blackburn

(57) ABSTRACT

Imnunoassays for detecting hepatitis C virus protein and immune complexes between hepatitis C virus protein and antibodies in biological samples, methods of screening blood products for hepatitis C virus, and kits employed therefor are provided.

15 Claims, 3 Drawing Sheets

Assay Configurations

= Paramagnetic Particle

= Mouse Anti-Human IgG

= Polyclonal Antibody to HCV e1/e2

= HCV Positive Sample
Human IgG Anti-HCV Immunocomplex

= Mouse Monoclonal Antibody To HCV e2 Biotinylated

= Streptavidin Conjugated to DMAE

= Ag

HEPATITIS C VIRAL ANTIGEN IMMUNOASSAY DETECTION SYSTEMS

This is a U.S. national application of PCT/US00/20214, filed 25 Jul. 2000, which claims benefit of application 60/146,079, filed 28 Jul. 1999.

FIELD OF THE INVENTION

The present invention is related generally to immunoassays for detecting hepatitis C virus and specifically to methods of detecting hepatitis C virus in biological samples, methods of screening blood products for hepatitis C virus, and kits therefor.

BACKGROUND OF THE INVENTION

Hepatitis C virus (HCV) was first identified and characterized as the primary cause of post transfusion non-A, non-B hepatitis (NANBH) by Houghton, et al. In addition to providing substantial information concerning HCV, Houghton, et al., and their collaborators have disclosed a number of general and specific immunological reagents and methods. See, e.g. Houghton, et al., EPO Pub. No. 318,216; Houghton, et al., EPO Pub. No. 388, 232; Choo, et al., *Science*, 1989, 244, 359–362; Kuo, et al., *Science*, 1989, 244, 362–364; Takeuchi, et al., *J. Gen. Virol.*, 1990, 71, 3027–3033; Takeuchi, et al., *Gene*, 1990, 91, 287–291; Takeuchi, et al., *Nucl. Acids Res.*, 1990, 18, 4626; Miyamura, et al., *Proc. Natl. Acad. Sci. USA*, 1990, 87, 983–987: Saito, et al., *Proc. Natl. Acad. Sci. USA*, 1990, 87, 6547–6549; Choo, et al., *Proc. Natl. Acad. Sci. USA*, 1991, 88, 2451–2455; Han, et al., *Proc. Natl. Acad. Sci. USA*, 88, 1711–1715; Houghton, et al., *Hepatology*, 1991, 14, 381–388; and Weiner, et al., *Proc. Natl. Acad. Sci. USA*, 1992, 89, 3468–3472. These publications provide the art with an extensive background on HCV generally, as well as the manufacture and uses of HCV polypeptide immunological reagents. For brevity, therefore, the disclosure of these publications in particular are incorporated herein by reference in their entirety.

Others have readily applied and extended the work of Houghton, et al. See, e.g. Highfield, et al., UK Pat App. 2,239,245 (The Welcome Foundation Ltd.); Wang, EPO Pub. No. 442,394 (United Biomedical Inc.); Leung, et al., EPO Pub. No. 445,423 (Abbott Laboratories); Habits, et al., EPO Pub. No. 451,891 (Akzo N.V.); Reyes, et al., PCT Pub No. WO 91/15516 (Genelabs Inc.); Maki, et al., EPO Pub. No. 468,657 (Tonen Corp.); and Kamada, et al., EPO Pub. No. 469,348 (Shionogi Seiyaku K.K). See also, Matsuura, et al., *J. Virology*, 1992, 66, 1425; Kato, et al., *Proc. Natl. Acad. Sci. USA*, 1990, 87, 9524–9528; Takamizawa, et al., *J. Virol.*, 1991, 65, 1105–1113; Chiba, et al., *Proc. Natl. Acad. Sci. USA*, 1991, 88, 4641–4645; Harada, et al., *J. Virol.*, 1990, 65, 3015–3021; Hijikata, et al., *Proc. Natl. Acad. Sci. USA*, 1991, 88, 5547–5551; Okamoto, et al., *Jpn. J. Exp. Med*, 1990, 60, 167–177; Yuasa, et al., *J. Gen. Virol.*, 1991, 72, 2021–2024; and Watanabe, et al., *Int. J. Cancer*, 1991, 48, 340–343.

Sensitive, specific methods for screening and identifying carriers of HCV and HCV-contaminated blood or blood products, as well as monitoring patients undergoing treatment, are important advances in medicine. Post-transfusion hepatitis (PTH) occurs in approximately 10% of transfused patients, and HCV has accounted for up to 90% of these cases. The major problem in this disease is the frequent progression to chronic liver damage (25–55%) relative to other hepatitises, such as type B.

Patient care as well as the prevention of transmission of HCV by blood and blood products or by close personal contact require reliable diagnostic and prognostic tools, such as, for example, HCV antibodies, to detect proteins related to HCV infection. Such antibodies are also useful as agents for monitoring treatment regimens for patients with HCV. Since HCV is a relatively new agent, a continuing need exists to define additional immunological reagents that will allow further study of the clinical course of disease and the epidemiology of HCV in the population.

Current methodology for detecting HCV focuses on detecting HCV-specific antibodies. See, for example, Hada, et al., *Acta Med. Okayama*, 1992, 46, 365–70; Miyamura, et al., EPO Pub. No. 0537626; Lok, et al., *Hepatology*, 1993, 18, 497–502; Wang, et al., *Vox Sang*, 1992, 62, 21–4; Kleinman, et al., *Transfusion*, 1992, 32, 805–813; Leon, et al., *Vox Sang*, 1996, 70, 213–16; Lesniewski, et al., *J. Med. Virol.*, 1995, 45, 415–22; and Inoue, et al., *J. Gen. Virol.*, 1992, 73, 2151–54. A major disadvantage to detecting antibodies which react with HCV is that seroconversion has already occurred and the patient may already have a well-established viral infection. Alternatively, if an individual is determined to be HCV antibody reactive, it may simply mean that the individual has been exposed to HCV sometime in the past and may not be presently infected.

Other methods for detecting HCV comprise using PCR. See, for example, Francois, et al., *J. Clin. Microbiol.*, 1993, 31, 1189–93. HCV envelope proteins have also been detected by immunohistochemical analysis of hepatocytes in patients with chronic liver disease. However, these assays do not easily lend themselves to a clinical setting. Hiramatsu, et al., *Hepatology*, 1992, 16, 306–311.

Other methods also are directed to detecting HCV core protein. See, for example, Orito, et al., *Gut*, 1996, 39, 876–80 and Kashiwakuma, et al., *J. Immunol. Methods*, 1996, 190, 79–89. These methods include a protein-capture fluorescence enzyme immunoassay (FEIA), a traditional sandwich ELISA assay, using monoclonal antibodies reactive with recombinant HCV core protein. The method consists of using one monoclonal antibody coated on a solid phase as a capture antibody and beta-D-galactosidase conjugated monoclonal antibody as the antigen detection signal antibody. These assays, however, require very tedious sample preparation procedures including, for example, polyethyleneglycol precipitation, NaOH denaturation, retritration of the sample to neutral pH and addition of Triton X-100 to the sample preparation prior to starting the assay. Such assays are not convenient in the clinical setting. Indeed, what is required is an easy, fast immunoassay for detection of HCV antigens.

Applicants have developed an immunoassay system which can detect HCV envelope antigens, E1 and E2, without tedious sample preparation procedures. Applicants' invention provides a means to detect free HCV antigens prior to seroconversion, antigen disappearance after acute infection, and/or interferon therapy and, thus, is useful as a diagnostic and for blood screening and evaluating the effectiveness of drug treatment. Thus, Applicants' invention is a significant improvement for detecting HCV in biological samples.

SUMMARY OF THE INVENTION

The present invention is directed to methods for detecting hepatitis C virus in biological samples comprising contacting the sample with an anti-human antibody and at least one monoclonal anti-hepatitis C virus envelope protein antibody under conditions that allow an immunologic reaction between the antibodies and the sample, and detecting the presence of immune complexes of the antibodies and the envelope protein.

The present invention is also directed to methods for detecting hepatitis C virus in a biological sample comprising contacting an anti-human antibody attached to a solid phase with a polyclonal anti-hepatitis C virus envelope protein antibody, contacting the sample to the polyclonal antibody, contacting the sample with at least one detectably-labeled, monoclonal anti-hepatitis C virus envelope protein antibody under conditions that allow an immunologic reaction between the antibodies and the sample, and detecting the presence of immune complexes of the antibodies and the envelope protein and/or the presence of free envelope protein.

The present invention is also directed to methods of screening blood components or blood for hepatitis C virus prior to the use of such blood or blood component to prepare blood products comprising reacting a body component from a potential donor with an anti-human antibody and at least one monoclonal anti-hepatitis C virus envelope protein antibody under conditions that allow an immunologic reaction between the antibodies and the body component, detecting the presence of immune complexes formed between the antibodies and hepatitis C virus envelope proteins, and discarding any blood or blood component from the donor if the complexes are detected.

The present invention is also directed to kits for detecting hepatitis C virus in a biological sample comprising an anti-human antibody, at least one monoclonal anti-hepatitis C virus envelope protein antibody, control standards, and instructions for use of the kit components.

DETAILED DESCRIPTION OF PREFERRED EMBODIMENT

Figure 1A:
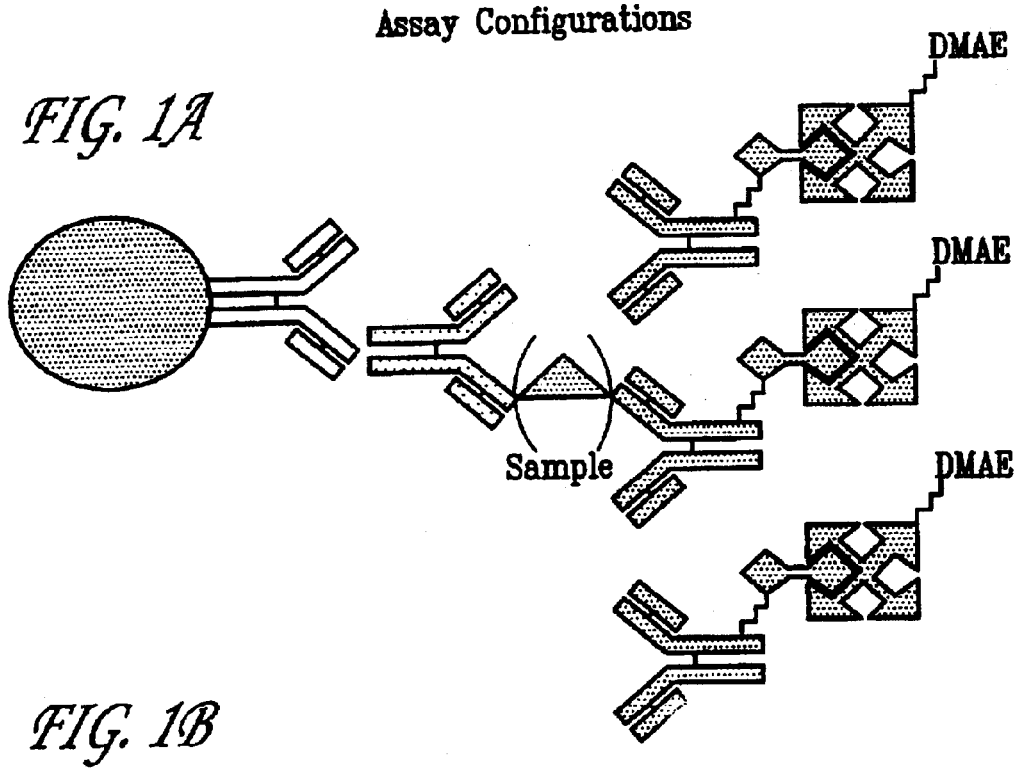
FIGS. 1A, 1B, 1C represent preferred assay configurations of the present invention.

The practice of the present invention will employ, unless otherwise indicated, conventional methods of virology, immunology, microbiology, molecular biology and recombinant DNA techniques within the skill of the art. Such techniques are explained fully in the literature. See, e.g., Sambrook, et al., *Molecular Cloning: A Laboratory Manual*, 2nd Ed., 1989; *DNA Cloning: A Practical Approach*, Vols. I & II, D. Glover, Ed.; *Methods In Enzymology*, S. Colowick and N. Kaplan, Eds., Academic Press Inc.; *Handbook of Experimental Immunology*, Vols I–IV, D. M. Weir and C. C. Blackwell, Eds., Blackwell Scientific Publications; and *Fundamental Virology*, 2nd Ed., Vols. I & I, B. N. Fields and D. M. Knipe, Eds., each of which is incorporated herein by reference in its entirety. In addition, antibodies are prepared following standard published protocols set forth in, for example, Harlow and Lane, 1988, Antibodies: A laboratory manual, Cold Spring Harbor, N.Y.: Cold Spring Harbor Laboratory Press, which is incorporated herein by reference in its entirety.

"HCV envelope protein" refers to a polypeptide or polypeptide analog (e.g., mimitopes) comprising an amino acid sequence (and/or amino acid analogs) defining at least one HCV epitope within an envelope protein. Typically, the sequences defining the epitope correspond to the amino acid sequence of an HCV protein (either identically or via substitution of analogs of the native amino acid residue that do not destroy the epitope). In general, the epitope-defining sequence will be 5 or more amino acids in length, more typically 8 or more amino acids in length, and even more typically 10 or more amino acids in length.

"Linear epitope" refers to a portion of an envelope protein that comprises a series of contiguous amino acids. The antibody binding portion preferably interacts with an epitope defined by 5 or more contiguous amino acids, more typically 8 or more contiguous amino acids, and even more typically 10 or more contiguous amino acids.

"Linear neutralizing epitope" refers to a linear epitope such that when an antibody is bound to the epitope, the antibodies block viral infection of the target cell. Antibodies reactive with these epitopes within an envelope protein are able to inhibit or abrogate viral infection of target cells.

"Conformational epitope" refers to epitopes formed by the three dimensional shape of the antigen (e.g., folding). The length of the epitope defining sequence can be subject to wide variations. Thus, the amino acids defining the epitope can be relatively few in number, but widely dispersed along the length of the molecule (or even on different molecules in the case of dimers, etc.), being brought into the correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

"E1" as used herein refers to a protein or polypeptide expressed within the first 400 amino acids of an HCV polyprotein, sometimes referred to as the E or S protein. In its natural form it is a 35 kD glycoprotein which is found in strong association with membrane. In most natural HCV strains, the E1 protein is encoded in the viral polyprotein following the C (core) protein. The E1 protein extends from approximately amino acid (aa) 192 to about aa 383 of the full-length polyprotein. The term "E1" as used herein also includes analogs and truncated forms that are immunologically cross-reactive with natural E1.

"E2" as used herein refers to a protein or polypeptide expressed within the first 900 amino acids of an HCV polyprotein, sometimes referred to as the NS1 protein. In its natural form it is a 72 kD glycoprotein that is found in strong association with membrane. In most natural HCV strains, the E2 protein is encoded in the viral polyprotein following the E1 protein. The E2 protein extends from approximately aa 384 to about aa 820. The term "E2" as used herein also includes analogs and truncated forms that are immunologically cross-reactive with natural E2.

The term "aggregate" as used herein refers to a complex of E1 and/or E2 containing more than one E1 or E2 monomer. E1:E1 dimers, E2:E2 dimers, and E1:E2 heterodimers are all "aggregates" within the scope of this definition. Aggregates may also include larger forms, and may have molecular weights in excess of 800 kD.

The phrase "biological sample" refers to a fluid or tissue of a mammal (e.g., an anthropoid, a human) that commonly contains antibodies or viral particles. Such components are known in the art and include, without limitation, blood, plasma, serum, spinal fluid, lymph fluid, secretions of the respiratory, intestinal or genitourinary tracts, tears, saliva, milk, white blood cells, and myelomas. Biological samples also include biological liquids. The term "biological liquid" refers to a fluid obtained from an organism. Some biological liquids are used as a source of other products, such as clotting factors (e.g., Factor VIII:C), serum albumin, growth hormone, and the like. In such cases, it is important that the source of biological liquid be free of contamination by virus such as HCV. Biological samples are also referred to as "body components."

The phrase "solid phase" refers to a solid body to which the anti-human antibody is bound covalently or by noncovalent means such as hydrophobic adsorption. The solid phases facilitate separation of the sample from the antibody after incubation. Preferred examples of solid phases that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunlon™)), diazotized paper, nylon membranes, activated beads, Protein A beads, magnetic latex particles (MLP), paramagnetic particles (PMP), and paramagnetic beads. For example, Dynatech Immunlon™ 1 or Immunlon™ 2 microtiter pit or 0.25 inch polystyrene beads (Precision Plastic Ball) can be used.

One aspect of the present invention is directed to methods for detecting hepatitis C virus in a biological sample. Numerous immunoassay formats can be used according to the present invention. The immunoassay format, however, must allow for interaction among the components, i.e., the antibodies and the proteins that may be present in the biological sample. A preferred immunoassay format is an ELISA antigen-capture assay described below in greater detail. Equivalent immunoassay formats, however, are known to those skilled in the art and are included within the scope of the invention.

Figure 1B:
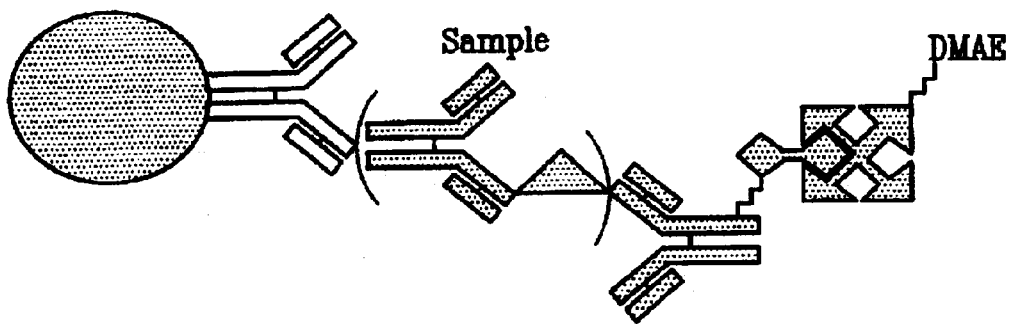

In a preferred embodiment of the invention, a method of detecting immune complexes of hepatitis C virus and antibody in a patient comprises contacting a biological sample with an anti-human antibody and at least one monoclonal anti-hepatitis C virus envelope protein antibody under conditions that allow an immunologic reaction between the antibodies and the sample, and detecting the presence of immune complexes of the antibodies and the envelope protein which may be present in the biological sample. A preferred embodiment of such an assay configuration is shown in FIG. 1B. This assay configuration can detect immune complexes comprising human anti-HCV antibodies bound to E1 and/or E2 proteins present in biological samples.

Figure 1C:
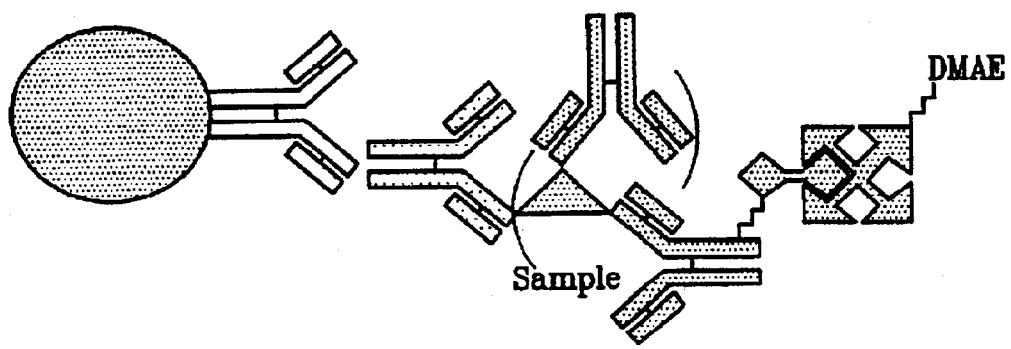
Figure 1D:
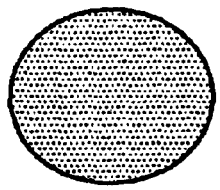
FIG. 1D shows preferred components in FIGS. 1A, 1B, and 1C.
Figure 1D:
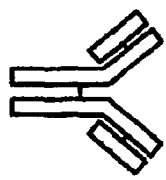
Figure 1D:
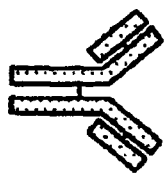
Figure 1D:
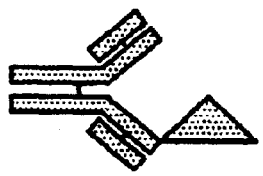
Figure 1D:
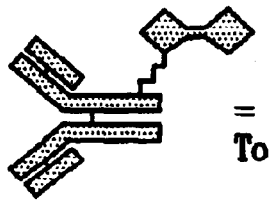
Figure 1D:
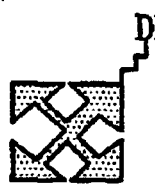
Figure 1D:

In another preferred embodiment of the present invention, a polyclonal anti-hepatitis C envelope protein antibody is contacted to the anti-human antibody, prior to contacting the biological sample, under conditions which allow an immunologic reaction between the anti-human antibody and the polyclonal anti-hepatitis C envelope protein antibodies. Preferred embodiments of such an assay configuration are shown in FIGS. 1A and 1C. This assay configuration can detect free envelope antigen (FIG. 1A) as well as immune complexes comprising human anti-HCV antibodies bound to E1 and/or E2 proteins (FIG. 1C).

The anti-human antibody can be commercially obtained from several sources including, for example, Boehinger Mannheim. Any anti-human antibody can be used in the present invention and can be derived from any animal or can be synthetically prepared. A preferred antibody is mouse anti-human IgGFe obtained from Walpole. Such antibodies are also able to bind primate antibodies, such as, for example, primate polycolonal anti-hepatitis C envelope protein antibodies. Preferably, the anti-human antibody is attached to a solid phase by standard techniques known to those skilled in the art. Preferably, the solid phase is a microtiter plate, paramagnetic particles or paramagnetic beads. Preferably, the anti-human antibodies are diluted to optimal concentration in PBS (pH 7.4) and coated on PMP.

The polyclonal anti-hepatitis C envelope protein antibodies can be generated using standard antibody generation techniques well known to those skilled in the art. These polyclonal antibodies preferably are recognized by the anti-human antibody. Accordingly, the polyclonal antibodies are preferably generated using primates such as, for example, chimpanzees. Preferably, as described below in greater detail, the primate is immunized with an e1/e2 heterodimer.

The anti-human antibody/primate polyclonal anti-HCV antibody complex bound to the solid phase is preferably contacted with the biological sample under conditions which allow an immunologic reaction between the polyclonal anti-HCV antibody and the free E1 and/or E2 proteins or E1 or E2 immune complexes, if present, in the biological sample. Such conditions will preferably be under physiologic temperature, pH and ionic strength and can take place in media such as, for example, phosphate buffered saline (PBS). Preferably, biological samples, which may be diluted from 0-fold to 1000-fold in sample diluent, are incubated for about 20 minutes to about 1 hour at 37° C. with the PMP-bound anti-human antibodies, then washed with wash buffer in connection with retention by a magnetic source.

After the biological sample is contacted with either the anti-human antibody (FIG. 1B) or the polyclonal anti-HCV envelope protein antibodies (FIGS. 1A or 1C), the biological samples further contacted with at least one monoclonal antibody which reacts with an epitope of either E1 or E2 under conditions which allow an immunologic reaction between the monoclonal anti-E1/E2 antibodies and the E1 and/or E2 proteins, if present, in the biological sample. Such conditions will preferably be under physiologic temperature, pH and ionic strength and may take place in media such as, for example, phosphate buffered saline (PBS). Preferably, the epitopes include an e2 conformational epitope, an e2 linear epitope, an e2 neutralizing epitope, an e1 conformational epitope, an e1 linear epitope, or an e1 neutralizing epitope. The neutralizing epitopes can be either linear or conformational. In preferred embodiments of the invention, the biological sample is contacted with a combination of different monoclonal antibodies reactive with these epitopes. The combination of monoclonal antibodies can include all of the possible combinations of the above-described epitopes. Monoclonal antibodies reactive with the above-described epitopes can be prepared by one skilled in the art using standard antibody production techniques. The mixture of the bound biological sample and monoclonal antibodies is preferably incubated for about 20 minutes to about 1 hour at 37° C., then washed with wash buffer in connection with retention by a magnetic source.

In order to prepare monoclonal antibodies to E1 and E2, the envelope antigens are prepared. The E1 domain, which is believed to correspond to the viral envelope protein, is currently estimated to span amino acids 192–383 of the HCV polyprotein (PCT Pub. No. WO91/5771, which is incorporated herein by reference in its entirety). Upon expression in a CHO system (glycosylated), it is believed to have an approximate molecular weight of 35 Kd as determined via SDS-PAGE. The E2 protein, previously called NS1, is believed to span amino acids 384–800 of the polyprotein and to also be an envelope protein. Upon expression in a CHO system (glycosylated), it is believed to have an apparent gel molecular weight of about 72 Kd. It is understood that these protein endpoints are approximations (e.g., the carboxy terminal of E2 could lie somewhere in the 750–820 amino acid region). It is also understood that the prototype isolate HCV1 sequence in the aforementioned PCT application is cited for illustrative purposes only and that any HCV isolate (see, e.g., references cited in the "Background" section) is a suitable source of E1 and/or E2 sequence for the practice of the present invention.

The E1 and E2 proteins used in the present invention to elicit antibody production can be full-length viral proteins, substantially full-length versions thereof, or functional fragments thereof (e.g., fragments which are not missing sequence essential to the formation or retention of a conformational epitope). The HCV proteins of the present invention can be made by any convenient method that provides the epitope of interest. For example, recombinant expression in mammalian or insect cells is a preferred method to provide secreted glycosylated E1 and/or E2 antigens in "native" conformation. However, it may also be possible, as it is known for proteins, to express the antigens in other recombinant hosts and renature the protein after recovery. It is also understood that chemical synthesis may also provide conformational antigen mimitopes that cross-react with the "native" antigen's conformational epitope.

Complexes of E1 and/or E2 (also called aggregates) containing more than one E1 or E2 monomer are also preferred antigens. E1:E1 dimers, E2:E2 dimers, and E1:E2 heterodimers are all antigens within the scope of this invention. Aggregates may also include larger forms, and may have molecular weights in excess of 800 kD.

Fusion polypeptides including a polypeptide in which the HCV antigen(s) are part of a single continuous chain of amino acids, which chain does not occur in nature, can also be used to prepare monoclonal antibodies. The HCV antigens may be connected directly to each other by peptide bonds or be separated by intervening amino acid sequences. The fusion polypeptides may also contain amino acid sequences exogenous to HCV.

Methods for preparing E1 and E2 antigens including those with native conformations are described in Spaete, et al., Virology, 1992, 188, 819–830, and in WO 92/08734 and in U.S. Ser. No. 07/758,880, which are incorporated herein by reference in their entirety. Generally, host cells are chosen that will allow the formation of native conformational epitopes within the expressed envelope proteins; these host cells may include, for example, animal cells, insect cells, yeast cells, and the like.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers, Nature, 1978, 273, 113), Rous sarcoma virus (RSV), adenovirus (ADV), and bovine papilloma virus (BPV). Mammalian cells may also require terminator sequences and poly A addition sequences; enhancer sequences which increase expression may be included, and sequences which cause amplification of the gene may also be desirable. These sequences are known in the art.

Vectors suitable for replication in mammalian cells are known in the art, and may include viral replicons, or sequences which ensure integration of the appropriate sequences encoding NANBV epitopes into the host genome.

A vector which is used to express foreign DNA, and which may be used in vaccine preparation is Vaccinia virus. In this case the heterologous DNA is inserted into the Vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid vectors that greatly facilitate the construction of recombinant viruses have been described (see, for example, Mackett, et al., J. Virol., 1984, 49, 857, Chakrabarti, et al., Mol. Cell Biol., 1985, 5, 3403; and Moss in GENE TRANSFER VECTORS FOR MAMMALIAN CELLS, Miller and Calos, eds., Cold Spring Harbor Laboratory, Cold Spring Harbor, N.Y., 1987, p. 10.). Expression of the HCV polypeptide then occurs in cells or individuals which are immunized with the live recombinant vaccinia virus.

The segment of HCV CDNA encoding the desired sequence is inserted into a Vaccinia vector. The polypeptide encoding sequence may be attached to a leader sequence. The leader sequence may be that for tissue plasminogen activator (TPA), or from another source, e.g., that for beta-globin. The heterologous polynucleotide may be inserted into a vaccinia vector which is a modified version of pSC11, due to the addition of a polylinker sequence which contains a cloning site.

In order to detect whether or not the HCV polypeptide is expressed from the vaccinia vector, BSC 1 cells may be infected with the recombinant vector and grown on microscope slides under conditions which allow expression. The cells may then be acetone-fixed, and immunofluorescence assays performed using serum which is known to contain anti-HCV antibodies to a polypeptide(s) encoded in the region of the HCV genome from which the HCV segment in the recombinant expression vector was derived.

Other systems for expression of E1 and E2 include insect cells and vectors suitable for use in these cells. These systems are known in the art, and include, for example, insect expression transfer vectors derived from the baculovirus Autographa californica nuclear polyhedrosis virus (AcNPV), which is a helper-independent, viral expression vector. Expression vectors derived from this system usually use the strong viral polyhedrin gene promoter to drive expression of heterologous genes. Currently the most commonly used transfer vector for introducing foreign genes into AcNPV is pAc373. Many other vectors, known to those of skill in the art, have also been designed for improved expression. These include, for example, pVL985 (which alters the polyhedrin start codon from ATG to ATT, and which introduces a BamHI cloning site 32 basepairs downstream from the ATT; See Luckow and Summers, Virology, 1989, 17, 31). Good expression of nonfused foreign proteins usually requires foreign genes that ideally have a short leader sequence containing suitable translation initiation signals preceding an ATG start signal. The plasmid also contains the polyhedrin polyadenylation signal and the ampicillin-resistance (amp) gene and origin of replication for selection and propagation in E. coli.

Methods for the introduction of heterologous DNA into the desired site in the baculovirus virus are known in the art. (See Summer and Smith, Texas Agricultural Experiment Station Bulletin No. 1555; Ju, et al. (1987); Smith, et al., Mol. & Cell Biol., 1983, 3, 2156–2165; and Luckow and Summers, *Virology*, 1989, 17, 31). For example, the insertion can be into a gene such as the polyhedrin gene, by homologous recombination; insertion can also be into a restriction enzyme site engineered into the desired baculovirus gene. The inserted sequences may be those which encode all or varying segments of the polyprotein, or other ORFs which encode viral polypeptides. The signals for posttranslational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequence from vertebrate cells which are effective in invertebrate cells are known in the art, for example, the human interleukin 2 signal (IL2$_s$) which is a signal for transport out of the cell, is recognized and properly removed in insect cells.

Once the E1 and E2 proteins have been prepared, such as by the methods described above, monoclonal antibodies to conformational epitopes and linear epitopes can be prepared using standard monoclonal antibody techniques. Monoclonal antibodies directed to conformational epitopes of E1 and E2 are prepared using intact, native E1 and E2 proteins. Monoclonal antibodies directed to linear epitopes of E1 and E2 are prepared using denatured E1 and E2 proteins. The presence or absence of a conformational epitope can be readily determined through screening the E1 or E2 protein with an antibody and comparing its reactivity to that of a denatured version of the antigen which retains only linear epitopes (if any). In such screening using polyclonal antibodies, it may be advantageous to adsorb the polyclonal serum first with the denatured E1 or E2 protein and see if it retains antibodies to the E1 or E2 protein. Preferably, the monoclonal antibody preparations are compositions wherein the desired antibody comprises at least 35% of the total protein component in the composition. The desired antibody preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition can contain other compounds such as carbohydrates, salts, lipids, solvents, and the like, without affecting the determination of the percentage purity as used herein.

Preferred monoclonal antibodies to conformational epitopes include, but are not limited to, 5E5/H7 (IgG1 anti-HCV e2 prepared from amino acids 1–967 of e1/e2in HeLa cells), 2A3/B12 (anti-HCV e2 prepared from amino acids 1–967 of e1/e2 in HeLa cells), 5E9/D10 (anti-HCV e2 prepared from amino acids 1–967 of e1/e2 in HeLa cells), 3F5/H6 (anti-HCV e2 prepared from amino acids 1–967 of e1/e2 in HeLa cells), and 291/A2 (IgG1 anti-HCV e2 prepared from amino acids 384–715 of e2 in CHO cells) available from Bio-Chilie, and 472.2.5 (anti-HCV e2 prepared from e2 HV peptide) available from Mimotopes, and 6A1 (IgG1 anti-HCV e2 prepared from amino acids 1–967 of e1/e2 in CHO cells; blocks binding to MOLT4 receptor) and 6A21 (IgG1; blocks binding to MOLT4 receptor) available from Biocine. Preferred monoclonal antibodies to linear epitopes include, but are not limited to, 3D5/C3 (IgG1 anti-HCV e1 prepared from amino acids 1–967 of e1/e2 in HeLa cells) and 3E5-1 and 3E5-2 (IgG1 anti-HCV e2 prepared from amino acids 404–661 of e2 in insect cells) available from Bio-Chilies. Additional monoclonal antibodies can be prepared as described herein using methods well known to the skilled artisan.

The presence of the immune complexes between the envelope proteins in the biological sample and the monoclonal antibodies is detected using any number of means widely known to the skilled artisan. For example, detectably labeled secondary antibodies can be added to the sample mixtures which react with the monoclonal antibodies. Preferably, the monoclonal anti-hepatitis envelope protein antibodies are detectably labeled. The labels may be, for example, enzymatic, fluorescent, chemiluminescent, radioactive, or dye molecules. Assays which amplify the signals from the immune complex are also known; examples of which are assay which utilize biotin and avidin, and enzyme-labeled and mediated immunoassays, such as ELISA assays.

In preferred embodiments of the invention, biotin-streptavidin is used to detect the immune complexes. Preferably, the mouse monoclonal antibodies are biotinylated. Streptavidin conjugated to DMAE is added to the biological sample mixture in order to detect the biotinylated monoclonal antibodies. In other preferred embodiments of the invention, the sensitivity of the detection system can be enhanced by adding streptavidin conjugated to horseradish peroxidase (HRP) and subsequently adding secondary antibodies directed to HRP and conjugated to DMAE. A preferred secondary antibody is goat anti-HRP conjugated to DMAE. Other suitable detectable labels can be substituted for DMAE as known to those skilled in the art.

Another aspect of the present invention is directed to a method for screening blood components or blood for hepatitis C virus prior to the use of such blood or blood component to prepare blood products. In preferred embodiments of the invention, the method comprises reacting a body component from a potential donor with an anti-human antibody and at least one monoclonal anti-hepatitis C virus envelope protein antibody under conditions that allow an immunologic reaction between the antibodies and the body component and detecting the presence of immune complexes formed between the antibodies and hepatitis C virus envelope proteins. Preferably, any blood or blood component from the donor is discarded if the complexes are detected. The method of screening blood and blood products is essentially the same as for detecting the presence of HCV in biological samples.

In cases of a positive reactivity to the HCV antigen, it is preferable to repeat the immunoassay to lessen the possibility of false positives. For example, in the large scale screening of blood for the production of blood products (e.g., blood transfusion, plasma, Factor VIII, immunoglobulin, etc.), "screening" tests are typically formatted to increase sensitivity (to insure no contaminated blood passes) at the expense of specificity; i.e., the false-positive rate is increased. Thus, it is typical to only defer for further testing those donors who are "repeatedly reactive"; i.e., positive in two or more runs of the immunoassay on the donated sample.

The present invention is also directed to using the antibodies of the invention in connection with the HCV e1 and/or e2 detection system described herein to monitor treatment of individuals infected with HCV. An individual having HCV, for example, can be receiving conventional therapy, i.e., interferon treatment. Such individuals, at some time in the treatment course, would be expected to undergo a relapse in HCV due to, for example, clearance of interferon or other drugs from the individual's body. One skilled in the art can monitor the amount of HCV e1 or e2 protein in the individual by the methods described above and be able to predict when such relapse may occur sooner than would be possible using currently available techniques for detection of HCV which focus on antibody detection. Thus, one skilled in the art would be able to begin a second round of drug therapy at an earlier date.

The present invention is also directed to kits for detecting hepatitis C virus in a biological sample. The kits preferably comprise anti-human antibody, at least one monoclonal anti-hepatitis C virus envelope protein antibody, and antibody control standards. Other kit components, such as, for example, instructions for use of the kit components can also be included. Preferred kits optionally comprise polyclonal anti-hepatitis C virus envelope protein antibody. Preferably, the anti-human antibody is attached to a solid phase. In preferred kits, the monoclonal antibody reacts with an epitope selected from the group consisting of an e2 conformational epitope, an e2 linear epitope, an e2 neutralizing epitope, e1 conformational epitope, an e1 linear epitope, and an e1 neutralizing epitope. Other preferred kits comprise a plurality of monoclonal antibodies which react with an e2 conformational epitope, an e2 linear epitope, an e2 neutralizing epitope, e1 conformational epitope, an e1 linear epitope, an e1 neutralizing epitope, or a combination thereof. Preferably, the monoclonal antibody is detectably labeled as described above.

The following examples are intended to illustrate the invention and are not intended to limit the invention in any manner.

EXAMPLES

Example 1

Construction of PSC59 Poly

The HCV sequence used for the production of E1 and E2 was isolated from plasmid pC5P-1 as a StuI partial/BglII fragment. This fragment extends from the first methionine of HCV-1 polyprotein to aspartic acid at position 966. The domains included as the nucleocapsid, C, both putative envelope glycoproteins, E1 and E2, and a truncated form of NS2, respectively. In addition, the fragment also contains about 60 bp corresponding to that portion of the 5'-untranslated region of the HCV genome. One skilled in the art can also prepare other fragments containing portions of E1 and E2 as desired.

The fragment was treated with Klenow polymerase to create blunt ends, and then cloned into the StuI site of a vaccinia vector, PSC59 (obtained from Dr. B. Moss at the National Institutes of Health, Bethesda, Md.); other vectors can be used, however. As a result of the ligation into the polylinker sequence of the vector, the C'-terminus of the NS2 region contains an additional Pro-Tyr sequence.

Example 2

Preparation of Stocks of Vaccinia Virus Encoding the HCV Polyprotein Fragment Including E1 and E2

The screening for recombinant Vaccinia virus was carried out essentially as described by Mackett et al. in DNA Cloning, Vol. II (Ed. D. M. Glover, IRL Press, Oxford, England, 1985, pp. 191–211). More specifically, a confluent monolayer (6 cm dish) of African green monkey kidney cells, BSC40, was infected with wild type Vaccinia virus (WR strain) at a multiplicity of infection (MOI) of 0.05. After a 2 hour incubation at 37° C., the cells were transfected with 25 µg of PSC59 poly DNA using the calcium phosphate method. After 4 hours of incubation, the medium was changed to normal medium, and the cells were incubated for an additional 48 hours at 37° C. The cells were recovered by scraping them from the dish, and the virus was released by 3 cycles of freezing-thawing, and the released virus in the cell lysate were stored at −80° C.

In order to screen for recombinant virus, a confluent monolayer of human 143 TK⁻ cells were infected for 2 hours with the cell lysate in 10-fold serial dilutions. After removal of the inoculum, 1% agarose in serum medium containing 25 µg/ml 5-bromodeoxyuridine was added, and the cells were incubated 72 hours at 37° C. Plaques were visualized by overlaying the cell layer with 1% agarose plus 0.01% neutral red, and incubating the cells overnight at 37° C. The agarose overlay was then carefully removed, and the cell layer was blotted with a master nitrocellulose filter (S&S, BA85, 0.45 µm). A replica plate of the master filter was made, and probed with a $^{32}$P-labeled hybridization probe to the HCV sequence. Positive plaques were isolated from the master filter, placed in 0.5 ml serum-free medium, and sonicated twice for 30 seconds. The screening process was repeated twice to plaque purify the virus.

In order to propagate the recombinant Vaccinia virus, ten dishes (150 cm²) of BSC40 cells were infected with the viral stock at a MOI of 0.5. The infection was carried out for 2 hours at 37° C., and the viral stock replaced with fresh medium. After 72 hours the cells were harvested, suspended in 10 mM Tris HCl, Ph 9.0, and homogenized in a Wheaton dounce tissue grinder. Cell debris was removed by centrifugation, the supernatants were typsinized and sonicated, and aliquots of the viral suspensions were stored at −80° C.

Example 3

Production of E1/K2 Antigens

One liter of Hela S3 spinner cells were brown in a spinner flask to a density of 10⁶ cells per ml. The cells were infected with the recombinant Vaccinia virus encoding the HCV polyprotein fragment using a MOI of 1.0, incubated overnight, harvested, and stored as a cell pellet at −80° C.

The E1/E2 expression product was purified by lysing the cells in hypotonic buffer, followed by extraction in a buffer containing nonionic detergent. The cellular extract was chromatographed tough a lectin (GNA) agarose column. The desired proteins were eluted from the column with methyl-α-D-mannopyranoside (Sigma Corp.). The eluted fractions were monitored for E1 and E2 by Western blots using a specific antiserum raised against E1 or E2. The fractions containing the antigens were pooled and concentrated on a S-Sepharose column (Pharmacia). The purity of the final product was about 70%.

The E1 (130aa) and E2 (251aa) proteins can also be expressed as internal antigens within yeast, *S. cerevisiae*, as C-terminal fusions with human superoxide dismutase (SOD) using methods described previously by Kuo et al., *Science*, 1989, 244, 362–364, and Cousens et al., *Gene*, 1987, 61, 265–272, each of which is incorporated herein by reference in its entirety. Following cell breakage and centrifugation, the insoluble SOD fusion polypeptides were extracted from the cell pellets using either 5 M urea or 1% SDS and purified using either gel filtration or a combination of ion-exchange chromatography (Q- and S-sepharose) and gel filtration chromatography (Sephacryl S-300 HR).

The HCV native E1 and E2 antigen can also be purified from the endoplasmic reticulum of recombinant Vaccinia vis (rvv)-infected cells that contain the full length HCV E1 and E2 genes. Purification can be accomplished by affinity chromatography, followed by ion exchange chromatography under non-denaturing conditions as described in, for example, WO 92/08734 and in U.S. Ser. No. 07/758,880, each of which are incorporated herein by reference in its entirety.

The native HCV E2 antigen, CHO-e2, can also be prepared essentially according to Spaete et al., Virology, 1992, 188, 819–830, which is incorporated herein by reference in its entirety. More specifically, the mammalian CHO cell line producing CHO-e2 antigen is constructed from a plasmid containing an HCV-1 sequence encoding Ala383 to Glu661. The plasmid is then transfected into CHO cells to generate a stable line expressing full length e2 (also called e2/ns1) antigen. Clones exhibiting high expression are selected and expanded in roller bottles by growth in DME/H21 with 10% dialyzed fetal calf serum and the usual supplements plus 1.6 $\mu$M Methotrexate. The culture medium supernatant is harvested, and used for the purification of the CHO-e2 antigen. The purification scheme includes affinity and ion exchange chromatography under non-denaturing conditions.

In order to perturb the native e2 putative conformational epitopes, denatured CHO-e2 is prepared by addition of DL-dithiothreitol (DTT) to a final concentration of 10 mM, 0.2% sodium dodecyl sulfate (SDS), and boiled at 100° C. for 5 minutes. All purified recombinant HCV antigens are at least 90% pure by SDS polyacrylamide gel analysis and staining with Coomassie blue.

Example 4

Detection Assay for Recombinant CHO-e2 Antigen

The sensitivity of a preferred detection assay was measured using recombinant CHO-e2 antigen. Briefly, a polyclonal chimp anti-HCV e1/e2 antibody/mouse anti-human IgG/PMP complex was contacted with recombinant HCV e2 produced in CHO cells as described above. A plurality of monoclonal anti-HCV envelope protein antibodies (291/A2, anti-e2 conformational; 1G2A7, anti-e2 neutralizing; and 3B5-2, anti-e2 linear) at 100 ng per assay were contacted to the complex. The monoclonal antibodies were labeled with biotin and the streptavidin system was used to measure binding. Typical results are shown in Table 1. The data indicates that the assay can detect CHO e2 antigen at concentrations as low as 1.95 ng/ml.

TABLE 1

| ng/ml CHO e2 | s(RLU) | s/n |
|---|---|---|
| 500 | 1,048,879 | 374.2 |
| 250 | 528,574 | 188.6 |
| 125 | 298,991 | 106.7 |
| 62.5 | 147,963 | 52.8 |
| 31.3 | 80,558 | 28.8 |
| 15.6 | 43,166 | 15.4 |
| 7.81 | 23,254 | 8.3 |
| 3.91 | 14,060 | 5.0 |
| 1.95 | 8,870 | 3.2 |
| 0 | 2,803 | 1 | s/n is the sensitivity (s) in relative light units (RLU) divided by the average negative value (s at 0 ng/ml of e2).

Example 5

Detection Assay for HCV With Clinical Biological Samples

A preferred detection assay which detects HCV e2 was compared to a detection assay which detects anti-HCV antibodies. Biological samples (serial bleeds) were obtained from two patients at several time points, for example, on 4/17 (I-1), 5/10 (I-2), 5/24 (I-3), 6/8 (I-4), 6/28 (I-5), 7/19 (I-6), and 12/28 (I-7). Patient I was an individual who had not yet seroconverted. Patient Y had already seroconverted. Each sample was examined for the presence of HCV e2 protein (Protein Assay) or for the presence of anti-HCV antibodies (Antibody Assay). For the Antibody Assay, CHO e2 protein linked to a solid phase was used to capture human anti-HCV antibodies that were present in the biological samples. A biotinylated monoclonal anti-human IgG/streptavidin system was used to detect the presence of the human anti-HCV antibodies. For the Protein Assay, solid phase linked to an anti-human IgG linked to a polyclonal anti-e1e2 antibody, as described above, was contacted with the biological sample. This system is able to detect free HCV antigen as well as HCV antigen/human Ig immunocomplexes. A biotinylated anti-e2 antibody, such as, for example, a combination of 3E5-2 and 291/A2, was used along with streptavidin to detect the presence of the HCV e2 protein. Typical results are shown in Table 2 (Antibody Assay), Table 3 (Protein Assay) and Table 4 (Standard Controls).

TABLE 2

Antibody Assay

| Patient/Sample | s (RLU) | s/n |
|---|---|---|
| I-1 | 3865 | 1.29 |
| I-2 | 4666 | 1.56 |
| I-3 | 6884 | 2.29 |
| I-4 | 5159 | 1.72 |
| I-5 | 4297 | 1.43 |
| I-6 | 8131 | 2.71 |
| I-7 | 19589 | 6.53 |
| Y-1 | 10842 | 3.61 |
| Y-2 | 32094 | 10.7 |
| Y-3 | 84715 | 28.24 |
| Y-4 | 93047 | 31.02 |
| Y-5 | 97343 | 32.45 |
| Y-6 | 75029 | 25.01 |
| Y-7 | 77524 | 25.84 |

TABLE 3

Protein Assay

| Patient/Sample | s (RLU) | s/n |
|---|---|---|
| I-1 | 3619 | 1.17 |
| I-2 | 2926 | 0.95 |
| I-3 | 3111 | 1.01 |
| I-4 | 2372 | 0.77 |
| I-5 | 2710 | 0.88 |
| I-6 | 108647 | 35.1 |
| I-7 | 7962 | 2.57 |
| Y-1 | 3265 | 1.05 |
| Y-2 | 3758 | 1.21 |
| Y-3 | 3496 | 1.13 |
| Y-4 | 3080 | 1.00 |
| Y-5 | 3034 | 0.98 |
| Y-6 | 3496 | 1.13 |
| Y-7 | 4805 | 1.55 |

TABLE 4

Standard Controls

| Standard CHO e2 (ng/ml) | s (RLU) | s/n |
|---|---|---|
| 500 | 729082 | 235.6 |
| 250 | 354724 | 114.6 |
| 125 | 179610 | 58.0 |
| 62.5 | 102241 | 33.0 |
| 31.3 | 55640 | 18.0 |
| 15.6 | 30246 | 9.8 |
| 7.81 | 17125 | 5.5 |
| 3.91 | 10872 | 3.5 |
| 1.95 | 7623 | 2.5 |
| 0 | 3095 | 1.0 |
| SAC | 40471 | 13.1 |
| NHS | 5960 | 1.9 | s/n is the sensitivity (s) in relative light units (RLU) divided by the average negative value (s at 0 ng/ml of e2).
SAC is a biological sample from a patient known to be infected with HCV and serves as a positive control.
NHS is normal human serum and serves as a negative control.

As can be seen from Tables 2 and 3, one skilled in the art using the HCV envelope protein detection system described above can detect HCV e2 protein earlier (bleed 6) than detection of human anti-HCV antibodies bleed 7).

Figure 2:
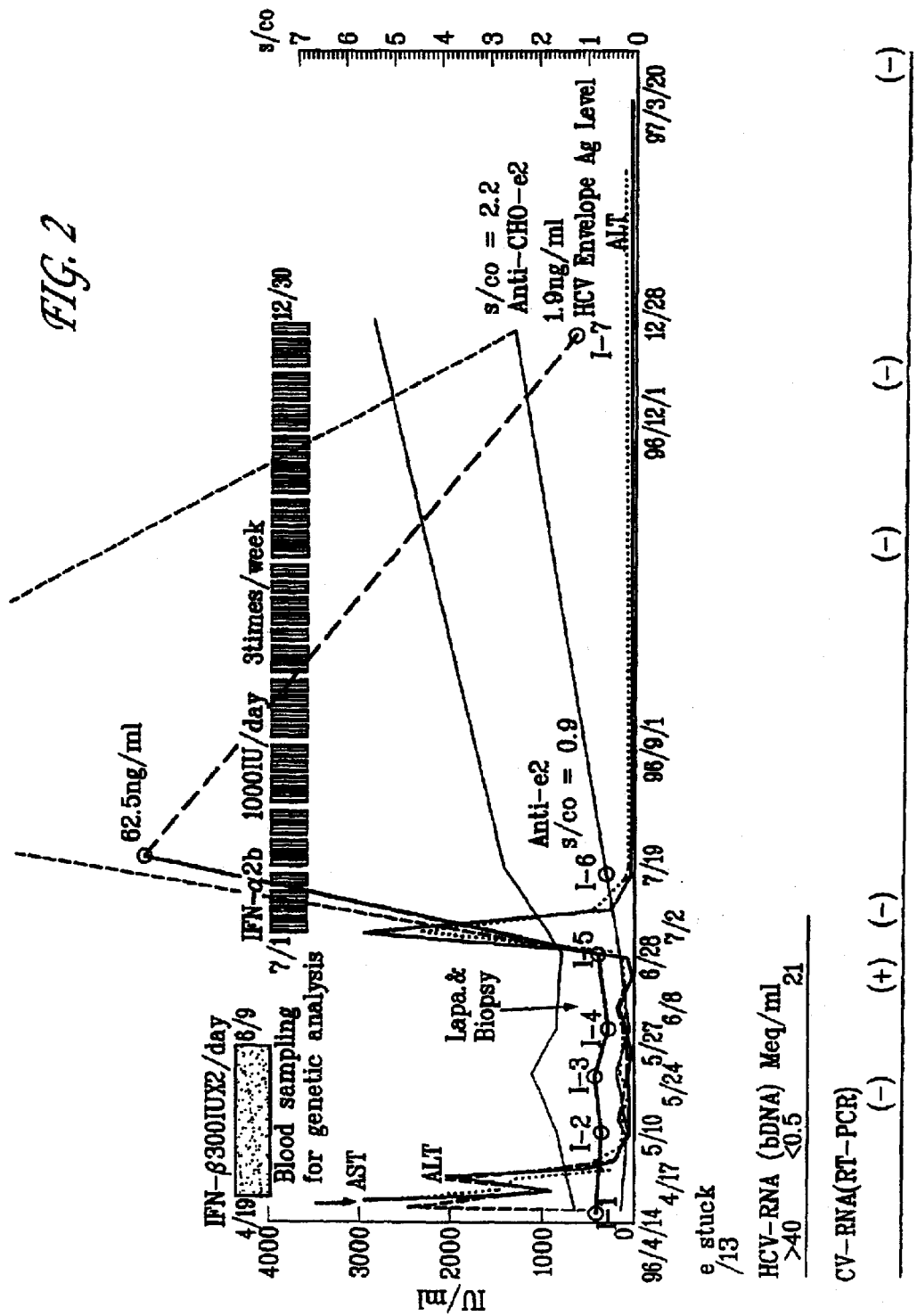
FIG. 2 is a graph showing the treatment regimen of a patient having HCV.

FIG. 2 is a graph representing the treatment regimen for patient I described above. Blood sample were also taken in order to detect the presence of AST and ALT, liver enzymes which indicate the presence of liver damage. The biological samples (bleeds) were examined for the presence of HCV protein (dashed line) and human anti-HCV antibodies (solid line). Also indicated in FIG. 2 is the timing of treatment with beta interferon and alpha interferon. As can be seen, as soon as liver damage was detected by monitoring the levels of AST and ALT, the patient received beta interferon (300 IU twice daily) for the period indicated. However, when the patient no longer received beta interferon treatment, HCV reinfection occurred as indicated by the presence of elevated levels of ALT and AST as well as by a dramatic increase in the detection of HCV envelope protein. In contrast, the increase in the level of human anti-HCV antibodies lagged dramatically. Upon detection of HCV envelope protein, the patient was promptly treated with alpha interferon which resulted in a subsidence in the HCV infection. Thus, the results depicted in FIG. 2 demonstrate that detection of HCV envelope protein is a dramatic improvement over detection of human anti-HCV antibodies in biological samples and also shows the impact of the detection system on monitoring convention HCV treatment.

Example 6

Detection Assay for Immunocomplexed HCV

The detection system described herein can also be used to detect immunocomplexed HCV envelope antigens. A preferred detection assay was performed to detect varying amounts of immunocomplexed HCV envelope antigen in several biological samples. Biological samples included I-6 (from Example 5; no immunocomplex), SAC (from Example 5; light immunocomplex), Y-7 (from Example 5; medium immunocomplex), and JP (sample from a patient with high seroconversion; heavy immunocomplex). Each sample was examined for the presence of HCV e2 protein (Protein Assay) as described above in Example 5 or for the presence of anti-HCV antibodies (Antibody Assay) as described above for Example 5. Typical results are shown in Table 5.

TABLE 5

| | Antibody Assay | | Protein Assay | |
|---|---|---|---|---|
| Biological Sample | s (RLU) | s/n | s (RLU) | s/n |
| I-6 | 8131 | 2.78 | 108647 | 51.8 |
| SAC | 19000 | 6.49 | 40471 | 19.3 |
| Y-7 | 73524 | 25.13 | 8963 | 4.3 |
| JP | 108770 | 37.17 | 1817 | 0.9 | s/n is the sensitivity (s) in relative light units (RLU) divided by the average negative value (s at 0 ng/ml of e2).

Example 7

Enhanced Detection Assay for HCV Envelope Proteins

The assay sensitivity of the detection system described herein can be amplified by applying signal amplification to a current assay format. For example, mouse monoclonal antibody to HCV e2 protein (5E5/H& adsorbed) linked to superparamagnetic latex particles (Estapor) was used to capture varying amounts of CHO e2 protein. Biotinylated polyclonal antibody to HCV e1e2 was used to detect the CHO e2 protein. A streptavidin-horse radish peroxidase (hrp) complex was used to bind to the biotinylated polyclonal antibody to HCV e1e2. In addition, a DMAE conjugated anti-hrp antibody (from various animals) was used to detect the streptavidin-horse radish peroxidase (hrp) complex, thus amplifying the signal. Typical results are shown in Table 6.

TABLE 6

| | goat anti-hrp | | rabbit anti-hrp | | mouse anti-hrp | | rat anti-hrp | |
|---|---|---|---|---|---|---|---|---|
| CHO e2 (ng/ml) | s (RLU) | s/n | s (RLU) | s/n | s (RLU) | s/n | s (RLU) | s/n |
| 500 | 766335 | 178.34 | 259952 | 116.41 | 3650 | 1.90 | 164487 | 52.87 |
| 250 | 415785 | 96.76 | 165889 | 74.29 | 4204 | 2.18 | 117810 | 37.87 |
| 125 | 317810 | 73.96 | 122430 | 54.83 | 3496 | 1.82 | 54162 | 17.41 |
| 62.5 | 127774 | 29.74 | 57242 | 25.63 | 1956 | 1.02 | 39747 | 12.78 |
| 31.3 | 70825 | 16.48 | 37961 | 17.00 | 2510 | 1.30 | 24224 | 7.79 |
| 15.6 | 48833 | 11.36 | 15169 | 6.79 | 2079 | 1.08 | 10657 | 3.43 |
| 7.81 | 24532 | 5.71 | 9317 | 4.17 | 3819 | 1.98 | 9440 | 3.03 |
| 3.91 | 8177 | 1.90 | 6699 | 3.00 | 3557 | 1.85 | 5606 | 1.80 |

TABLE 6-continued

| CHO e2 (ng/ml) | goat anti-hrp | | rabbit anti-hrp | | mouse anti-hrp | | rat anti-hrp | |
|---|---|---|---|---|---|---|---|---|
| | s (RLU) | s/n | s (RLU) | s/n | s (RLU) | s/n | s (RLU) | s/n |
| 1.95 | 5652 | 1.32 | 4481 | 2.01 | 3450 | 1.79 | 5159 | 1.66 |
| 0 | 4297 | 1.00 | 2233 | 1.00 | 1925 | 1.00 | 3111 | 1.00 | s/n is the sensitivity (s) in relative light units (RLU) divided by the average negative value (s at 0 ng/ml of e2).

The sensitivity can be increased even further by using paramagetic particles (PMP) instead of magnetic latex particles (MLP) and higher affinity anti-hrp second antibody conjugate (DMAE).

What is claimed is:

1. A method for detecting hepatitis C virus in a biological sample comprising the steps of:
   contacting a biological sample suspected of containing hepatitis C virus with an anti-human antibody and at least one monoclonal anti-hepatitis C virus envelope protein antibody under conditions that allow an immunologic reaction between said antibodies and said sample, and
   detecting the presence of immune complexes of said antibodies and said envelope protein, wherein detecting said immune complexes indicates the presence of hepatitis C virus.

2. The method of claim 1 wherein said anti-human antibody is attached to a solid phase.

3. The method of claim 2 wherein said solid phase is selected from the group consisting of microtiter plates, paramagnetic particles, and paramagnetic beads.

4. The method of claim 1 wherein said monoclonal antibody reacts with an epitope selected from the group consisting of an e2 conformational epitope, an e2 linear epitope, an e2 linear neutralizing epitope, an e1 conformational epitope, an e1 linear epitope, and an e1 linear neutralizing epitope.

5. The method of claim 1 wherein said at least one monoclonal antibody reacts with an e2 conformational epitope, an e2 linear epitope, an e2 linear neutralizing epitope, an e1 conformational epitope, an e1 linear epitope, an e1 linear neutralizing epitope, or a combination thereof.

6. The method of claim 1 wherein said monoclonal antibody is detectably labeled.

7. The method of claim 1 wherein said anti-human antibody is contacted with a polyclonal anti-hepatitis C virus envelope protein antibody prior to contact with a biological sample.

8. A method for detecting hepatitis C virus in a biological sample comprising:
   contacting an anti-human antibody attached to a solid phase with a polyclonal anti-hepatitis C virus envelope protein antibody;
   contacting a biological sample suspected of containing hepatitis C virus to said polyclonal antibody;
   contacting said sample with at least one detectably-labeled, monoclonal anti-hepatitis C virus envelope protein antibody under conditions that allow an immunologic reaction between said antibodies and said sample; and
   detecting the presence of immune complexes of said antibodies and said envelope protein, wherein detecting said immune complexes indicates the presence of hepatitis C virus.

9. A method of screening blood components or blood for hepatitis C virus prior to the use of such blood or blood component to prepare blood products comprising:
   reacting a body component from a potential donor with an anti-human antibody and at least one monoclonal anti-hepatitis C virus envelope protein antibody under conditions that allow an immunologic reaction between said antibodies and said body component;
   detecting the presence of immune complexes formed between said antibodies and hepatitis-C virus envelope proteins; and
   discarding any blood or blood component from said donor if said complexes are detected.

10. A kit for detecting hepatitis C virus in a biological sample comprising:
    an anti-human antibody;
    at least one monoclonal anti-hepatitis C virus envelope protein antibody;
    control standards; and
    instructions for use of the kit components.

11. The kit of claim 10 further comprising a polyclonal anti-hepatitis C virus envelope protein antibody.

12. The kit of claim 10 wherein said anti-human antibody is attached to a solid phase.

13. The kit of claim 10 wherein said monoclonal antibody reacts with an epitope selected from the group consisting of an e2 conformational epitope, an e2 linear epitope, an e2 linear neutralizing epitope, an e1 conformational epitope, an e1 linear epitope, and an e1 linear neutralizing epitope.

14. The kit of claim 10 comprising a plurality of monoclonal antibodies which react with an e2 conformational epitope, an e2 linear epitope, an e2 linear neutralizing epitope, an e1 conformational epitope, an e1 linear epitope, an e1 linear neutralizing epitope, or a combination thereof.

15. The kit of claim 10 wherein said monoclonal antibody is detectably labeled.

* * * * *